United States Patent [19]

Brånemark et al.

[11] Patent Number: 5,064,425
[45] Date of Patent: Nov. 12, 1991

[54] ANCHORING MEMBER FOR ANCHORAGE IN BONE TISSUE

[75] Inventors: Per-Ingvar Brånemark, Mölndal; Einar Jörgensen, Hisingskärra; Lars Jönéus, Gothenburg; Kjell O. Hagberg, Gothenburg; Lennart Lööf, Gothenburg; Carl A. Morenius, Mölndal, all of Sweden

[73] Assignee: The Institute for Applied Biotechnology, Gothenburg, Sweden

[21] Appl. No.: 84,229

[22] Filed: Aug. 11, 1987

[51] Int. Cl.$^5$ .................. A61F 5/04; A61C 8/00
[52] U.S. Cl. .......................... 606/72; 606/73; 433/174
[58] Field of Search .............. 606/59, 60, 62, 65, 606/69, 70, 71, 72, 73, 76, 77, 80; 128/60; 433/173–176

[56] References Cited

U.S. PATENT DOCUMENTS

| | | | |
|---|---|---|---|
| 3,067,740 | 12/1962 | Haboush | 606/72 |
| 3,488,779 | 1/1970 | Christensen | 606/71 |
| 3,846,846 | 11/1974 | Fischer | 606/72 |
| 4,145,764 | 3/1979 | Suzuki | 606/76 |
| 4,463,753 | 8/1984 | Gustilo | 606/62 |
| 4,468,200 | 8/1984 | Munch | 433/174 |
| 4,484,570 | 11/1984 | Sutter | 606/71 |
| 4,495,664 | 1/1985 | Blanguaert | 606/62 |
| 4,511,335 | 4/1985 | Tatum, Jr. | 606/62 |
| 4,535,487 | 8/1985 | Esper | 606/62 |
| 4,713,004 | 12/1987 | Linkow et al. | 433/174 |
| 4,851,008 | 7/1989 | Johnson | 606/62 |
| 4,878,915 | 11/1989 | Brantigan | 606/76 |
| 4,932,868 | 6/1990 | Linkow et al. | 433/174 |

FOREIGN PATENT DOCUMENTS

| | | |
|---|---|---|
| 0139052 | 5/1985 | European Pat. Off. . |
| 8523007 | 1/1985 | Fed. Rep. of Germany . |
| 3043336 | 12/1985 | Fed. Rep. of Germany . |
| 0332486 | 2/1971 | Sweden . |
| 1291470 | 10/1972 | United Kingdom . |

Primary Examiner—Robert A. Hafer
Assistant Examiner—Michael Brown
Attorney, Agent, or Firm—Pollock, Vande Sande & Priddy

[57] ABSTRACT

An elongate cylindrical body member is adapted for permanent anchoring of its lower end into bone tissue and constructed to support an attached device such as a tooth at its upper end. The body member has an external screw thread formed in its outer surface, and at least one cavity defined therein adjacent its bottom end. Each cavity forms at its intersection with the screw thread at least one cutting edge for self-tapping as the body member is screwed into the bone tissue. Such cavity defines a total volume within the outer surface of said body member sufficient to retain all the bone tissue material which is removed as a result of the self-tapping operation. The cavity stops short of the lowermost end of the body member so as to maintain the bottom end of the body member imperforate, whereby the screwing of the body member into a pre-formed receiving aperture formed in the bone tissue causes the resulting particles of bone tissue to collect in the cavity, thereby promoting the securing of the body member into the aperture, while the bottom of the receiving aperture remains free of the bone particles because of its imperforate bottom lower end member.

12 Claims, 2 Drawing Sheets

ANCHORING MEMBER FOR ANCHORAGE IN BONE TISSUE

The present invention relates to a screw-shaped anchoring member made of titanium for permanent anchorage in bone tissue. The anchoring member is particularly adapted for achieving the permanent anchorage of artificial teeth and tooth bridges in the jaw bone.

BACKGROUND ART

It is previously known to permanently anchor oral and extraoral prostheses in bone tissue. In order to avoid subsequent loosening of the prosthesis, a healing period is required during which there is a direct contact, i.e. an exact adaption, between the prosthesis and the bone tissue. Such a permanent, exact adaption which allows loading is called osseointegration. The possibility of such a long-term adaption and function in clinical practice of load-supporting artificial anchoring members was first indicated by Dr. Brånemark et al. They showed that screw-shaped anchoring members, so-called fixtures, of pure titanium were osseointegrated if a number of prerequisites were fulfilled. The osseointegration principle developed by Professor Brånemark et al has been used in clinical practice for 20 years with good results and has been described for instance in:

Brånemark/Zarb/Albrektsson: "Tissue-Integrated Prostheses, Quintessence Books, 1985.

The osseointegration principle is based not only on the use of an implant made of pure titanium but also on a specific operating technique which comprises installation of the titanium fixture in a first operation with a minimum of surgical trauma, a healing period for a specific period of time and without any direct load on the fixture, and a second operation in which the prosthesis part (abutment) is attached to the fixture, i.e. a two-stage operation with an intervening, unloaded healing period.

In order to achieve a good healing of the fixture within the bone tissue, a minimum of negative biological reactions should be induced, or even better, positive reactions only. The structure and the chemical composition of the fixture surface has been of a significant importance for these reactions.

In Swedish patent 7902035-0 it is illustrated how improved results can be achieved by a specific surface structure of the titanium material of the fixture. The surface layer of the fixture comprises a micro-pitted titanium dioxide in which the surface pits have a diameter of 10-1000 nm, preferably 10-300 nm. In Swedish patent application 8505158-9 is described a chemical composition for the titanium surface layer which has been made of specific advantage for the tissue reactions.

It is also important that the fixture has an adequate geometrical design in order to facilitate the requirement of an atraumatic surgical operation as well as a surface cleanliness. Swedish Patent specification 332 486 describes a bolt-shaped anchoring member with an external thread. The threaded part of the bolt is intended to be inserted into a hole drilled in the jaw bone and the bolt is provided with an internal thread for a permanent implantation of a dental anchoring member. The bolt is provided with a bore which is open at its forward end and provided with radially directed openings through the threads into the bore. The bolt also has a conical forward end part. The openings at the forward end part of the bolt are intended to facilitate the healing of the bolt into the jaw bone through in-growth of newly formed bone tissue through the openings to prevent the bolt from being screwed out.

As already mentioned the bolt is intended to be inserted into a hole drilled in the jaw bone. To satisfy the requirement of an atraumatic surgical operation technique, the preparation of the bone hole is made in several steps using drills with successively increasing drilling diameters as well as a series of screw taps. In order to achieve an atraumatic preparation of the fixture site, it is required that the temperature is maintained low, which involves low drilling speeds and adequate cooling by means of profuse irrigation with saline solution. The surface of the fixture must be very clean, which requires a careful cleaning after every operation step or the use of non-returnable instruments.

In order to facilitate the surgical method and decrease the number of instruments required for preparation of the bone tissue, it is previously known to provide the fixture with cutting edges for self-tapping when the fixture is installed in the bone tissue. In addition to forming the bone in-growth openings, a further machining of the end part of the fixture is therefore required in order to form such cutting edges. Examples of such self-tapping fixtures can be found in EP-A-139052 and DE-A-3043336.

The formation of the above-mentioned openings and cutting edges results in a complicated and expensive manufacturing method, often leaving burrs which are difficult to remove on inner surfaces. The cutting edges which have been extended to the forward end surface of the fixture may also damage the bone membrane during use.

SUMMARY OF THE INVENTION

The object of the present invention is to provide an anchoring member which fulfills the requirements of bone in-growth and provides a self-tapping function.

A further object of the invention is to provide an anchoring member which is designed in such a way that the risk of damaging the bone membrane during insertion is reduced.

The titanium anchoring member of this invention comprises an externally screw-threaded, generally cylindrical body. Directly communicating with the external cylindrical surface of the body is at least one cavity to allow in-growth of newly-formed bone tissue. The edges of the, or each, cavity form cutting edges to provide a self-tapping action when the anchoring member is screwed into bone tissue. In accordance with an important feature of this invention, the cavity or cavities are formed to have a total volume which is adapted to contain all the bone tissue material which is scraped off by the self-tapping action of the cutting edges as the anchoring member is screwed into place.

Another feature of the titanium anchoring member of this invention resides in the fact that the cavity or cavities communicate only with the external cylindrical surface of the body. This feature helps to minimize the risk of bone tissue material falling into the bone hole where it could hinder the osseointegration of the anchoring member during the healing period.

Furthermore, in the anchoring member of this invention, the risk of unintentional penetration of the bone membrane is reduced by forming the body with a forward end surface which is unbroken.

Specific and preferred embodiments of the invention provide anchoring members for permanently anchoring artificial teeth or tooth bridges in the jaw bone. In one such embodiment, a single cavity, of generally cruciform cross-section, i.e. providing four openings communicating with the exterior of the body, is provided by means of two mutually perpendicular through holes extending through the body perpendicularly to its longitudinal axis. An alternative embodiment of the anchoring member provides a plurality of discrete cavities, for example three cavities, distributed symmetrically about the periphery of the anchoring member body.

The anchoring member disclosed in the above-mentioned Swedish patent specification 332 486 is provided with a cavity or well 11, in which loose skeletal tissue material scraped off while the bolt is screwed into the bone hole can be collected. This well, however, is not adapted to accommodate the entire volume of such scraped off bone material. Moreover, this well 11 communicates not only with the cylindrical external surface of the bolt, but also opens downwards so that the scraped off bone material can fall down onto the bottom of the bone hole and disturb the osseointegration of the base of the anchoring member. These disadvantages can be avoided by following the teachings of the present invention.

The above and other objects, features and advantages of the invention will become apparent from the following description and appended claims, taken in conjunction with the accompanying drawings.

DESCRIPTION OF PREFERRED EMBODIMENTS

Figure 1:
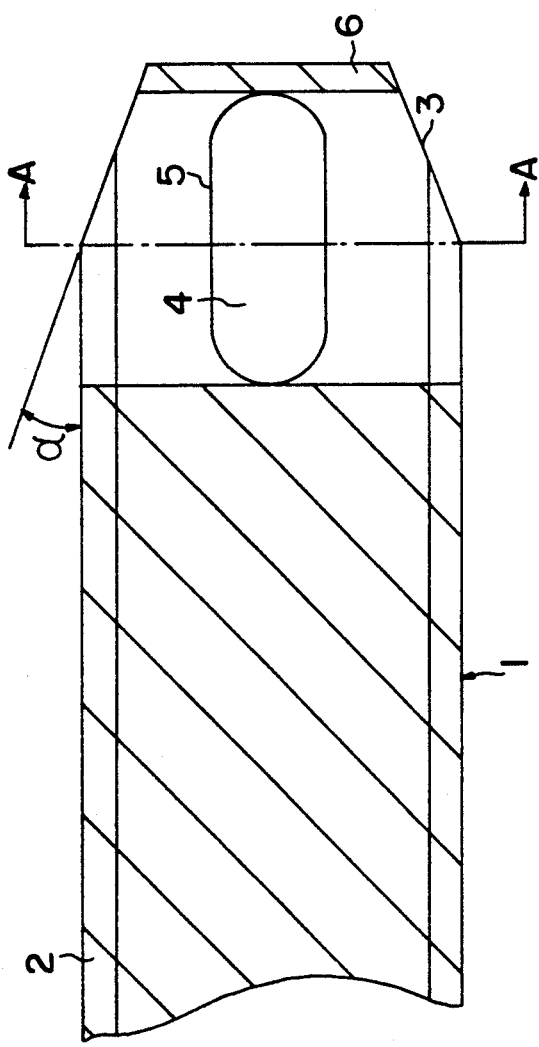

As illustrated in FIG. 1 the anchoring member, the so-called fixture, comprises a rigid, generally cylindrical body 1 formed with an external screw thread 2. In the drawings, only the forward or base portion of the body is shown. The body is particularly designed to be inserted into a bored hole in the jaw bone for permanent anchoring of artificial teeth and tooth bridges. The rear or neck portion of the body (not shown) is therefore intended to be attached with a distance element, coupling elements or the like. These elements form no part of this invention, however, and therefore will not be described here. The anchoring member is made of commercially pure titanium, with a surface structure and of a chemical composition preferably according to the above-mentioned Swedish patent specifications 7902035-0 and 8505158-9.

The body 1 has a conical, downwardly tapered (in use) forward part 3 to facilitate the insertion of the screw into the bored hole in the bone tissue. The cone angle α is suitably approximately 20°. The forward part 3 of the screw is provided with one or more cavities 4 on the cylindrical surface of the screw, in the illustrated embodiment there is a single cruciform-shaped cavity, as will now be described in more detail.

The edges of the cavity 4 on the cylindrical external surface form sharp cutting edges having a positive cutting angle, so that the screw is self-tapping when anchored in the bone tissue. The cavity 4 provides such a volume that the bone tissue material which is scraped off as the forward end 3 of the fixture advances into the bone hole can be entirely accommodated within the cavity. The cavity is closed apart from its four openings on the cylindrical surface of the body 1, which means that all scraped off bone tissue material is collected within the cavity and is stored there. The collected bone tissue material promotes newly formed bone tissue to grow in the cavity and, further, helps to prevent any tendency for the fixture to become unscrewed after insertion. The fixture has a plane, unbroken circular forward surface 6 without any openings.

The bone volume cavity is formed by two perpendicular through holes made in the cylindrical surface of the body and which are also perpendicular to the longitudinal axis of the body. The total volume of the cavity is then defined by the number of holes and the cross-sectional area of each hole. In the illustrated embodiment each hole has a longitudinal section with two straight edges parallel to the longitudinal axis of the body 1. It should be understood, however, that the holes could also be somewhat angled with respect to the longitudinal axis of the fixture body. A common feature for the hole configurations, however formed, is that the total volume of the cavity created should be such that the scraped off bone tissue material is accommodated within the cavity and stored there for the respective length of the fixture and also that both the cavity and its cutting edges are formed by one or more holes made in the cylindrical external surface of the fixture.

Figure 2:
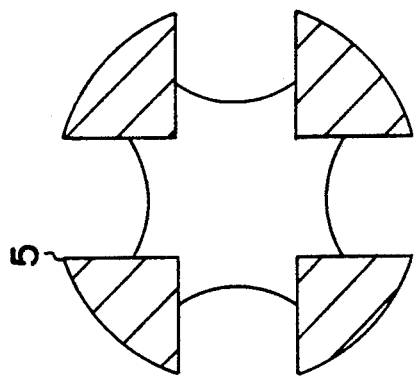
FIGS. 1 and 2 show, somewhat schematically and on an enlarged scale, a longitudinal section and a transverse section, respectively, through the forward end part of one embodiment of an anchoring member of this invention adapted for permanent anchorage of artificial teeth or tooth bridges in the jaw-bone.
Figure 4:
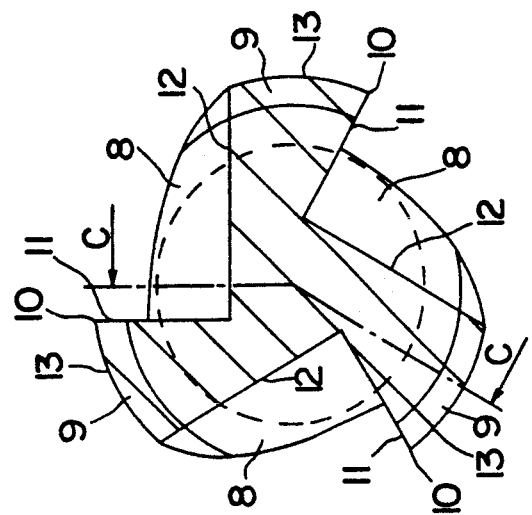
FIGS. 3 and 4 show, again somewhat schematically and on an enlarged scale, the corresponding sections through the forward end part of a second embodiment of an anchoring member of this invention for permanent anchorage of artificial teeth or tooth bridges in the jaw bone.
Figure 3:
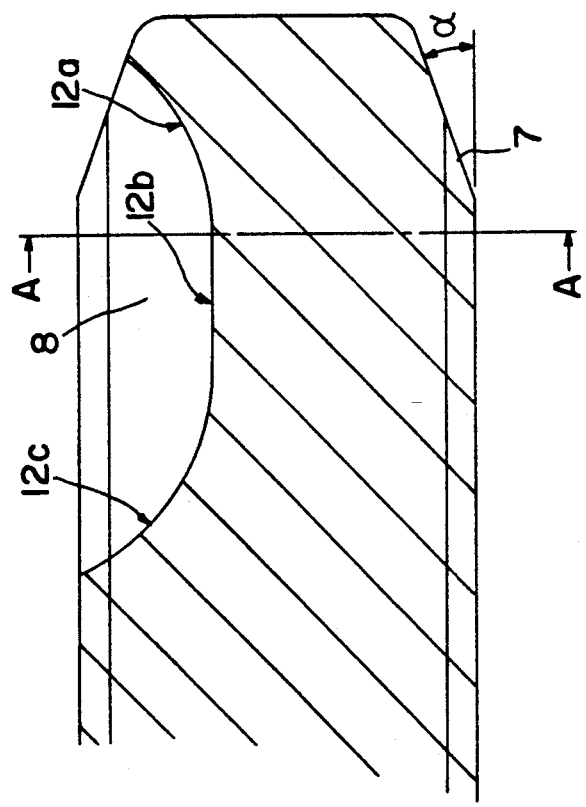

In FIGS. 3 and 4 is illustrated a further embodiment of a self-tapping fixture according to the invention. Like the fixture illustrated in FIGS. 1 and 2, this fixture also has a conical, downwardly tapered (in use) forward part 7, suitably with a cone angle α of approximately 20° to facilitate guiding of the fixture during the surgical procedure. The fixture also has an unbroken, plane forward surface to avoid unintentional penetration of the bone membrane. In this case, however, the fixture is provided with three separate cavities or bone volumes 8 which are symmetrically distributed about the periphery of the fixture body but not passing through the fixture. These cavities are formed by means of an external machining with only a small formation of burrs, which means a more efficient manufacturing method than the method of boring through holes, which is more complicated and expensive and can lead to burrs which are difficult to remove on inner surfaces.

Also in this case, the total bone volume of the cavities in the fixture is adapted to the fixture length so that all scraped off bone tissue material can be housed in the cavities. Each cavity is therefore much deeper than normal in conventional anchoring members. In the example illustrated in FIGS. 3 and 4, the depth of each bone volume cavity in the radial direction is approximately 50-80% of the radius of the fixture. The dimensions of the cavities in the longitudinal direction depends on the length of the fixture. As shown in FIG. 3, each cavity partially extends into the conical forward part 7 of the fixture, but not into the plane forward surface.

FIG. 4 is a sectional view of the fixture taken just above the conical tapered part of the body. The section shows the form of each of the bone cavities 8 and the cutting teeth 9 with cutting edges 10. Each bone cavity 8 is formed by a plane cutting surface 11 in which the cutting edge 10 has been moved over the center to provide positive cutting edges, and a concave clearance surface 12 which surfaces 11 and 12 are perpendicular. The clearance surface 12 includes a lower curved part 12a, a straight part 12b and an upper curved part 12c, see FIG. 3. Each cutting tooth 9 includes one cutting surface with a straight sharp cutting edge 10, a part 13 of the external cylindrical surface of the fixture body and the clearance surface 12.

Three separate bone cavities providing three cutting edges 10, as illustrated in FIGS. 3 and 4, give a good balance for the fixture when screwed into bone tissue. The invention is not limited, however, to the provision of just three such bone cavities.

The foregoing disclosures and description of the invention is illustrative and explanatory thereof, and various changes in the details of the illustrated apparatus may be made within the scope of the appended claims without departing from the spirit of the invention.

We claim:

1. An elongated generally cylindrical body member adapted for permanent anchoring of its lower end into bone tissue and constructed to support an attached device such as a tooth at its upper end, said body member having;
    (a) an external screw thread formed in its outer generally cylindrical surface;
    (b) at least one cavity defined therein adjacent its lower end, each said cavity forming at its intersection with said screw thread at least one cutting edge for self-tapping as said body member is screwed into the bone tissue;
    (c) said at least one cavity defining a total volume within the outer surface of said body member sufficient to retain all the bone tissue material which is removed as a result of the self-tapping operation; and
    (d) said generally cylindrical body member having a closed, imperforate bottom end and said at least one cavity stopping short of the lowermost end of said body member so as to maintain the bottom end of said body member imperforate;
    whereby the screwing of said body member into a preformed receiving aperture formed into said bone tissue causes the resulting particles of bone tissue to collect in said at least one cavity, thereby promoting the securing of said body member into said aperture, while the bottom of said receiving aperture remains free of said bone particles because of the closed imperforate bottom end of said member.

2. A body member according to claim 1, wherein said body member is made of titanium.

3. A body member according to claim 2, wherein a plurality of discrete cavities are distributed symmetrically about the periphery of said body member.

4. A body member according to claim 1, wherein said at least one cavity is formed by at least one through hole in said body member, said through hole having its longitudinal axis extending perpendicular to the longitudinal axis of said body member.

5. A body member according to claim 1, wherein said cavity is formed by two through holes extending through said body member, the longitudinal axes of said two through holes being perpendicular to each other and to the longitudinal axis of said body member, whereby said cavity has a cruciform cross-section.

6. A body member according to claim 5, wherein each said through hole has a longitudinal section defined by two straight, parallel edges in the longitudinal direction.

7. A body member according to claim 6, wherein said edges are substantially parallel to said longitudinal axis of said body member.

8. A body member according to claim 1, wherein a plurality of discrete cavities are provided distributed symmetrically about the periphery of said body member.

9. A body member according to claim 8, wherein each said cavity is defined by a plane cutting surface having a positive cutting angle and a concave clearance surface perpendicular to said cutting surface.

10. A body member according to claim 9, wherein three said discrete cavities are distributed symmetrically about the periphery of said body.

11. A body member according to claim 10, wherein a lower portion of said body member in which said cavities are distributed is made as a solid member.

12. A device adapted for permanent anchoring of its lower end into bone tissue and constructed to support an attached device such as a tooth at its upper end, said device comprising:
    (a) an elongated, generally cylindrical body member having a closed bottom end portion defining an imperforate forward surface;
    (b) an external screw thread formed in the outer surface of said body member;
    (c) at least one cavity defined therein adjacent its bottom end, each said cavity forming at its intersection with said screw thread at least one cutting edge for self-tapping as said body member is screwed into the bone tissue;
    (d) said at least one cavity defining a total volume within the outer surface of said body member sufficient to retain all the bone tissue material which is removed as a result of the self-tapping operation;
    (e) said at least one cavity stopping short of the lowermost end of said body member;
    (f) whereby the screwing of said body member into a preformed receiving aperture formed into said bone tissue causes the resulting particles of bone tissue to collect in said at least one cavity, thereby promoting the securing of said body member into said aperture, while the bottom of said receiving aperture remains free of said bone particles because of said closed, imperforate bottom end of said cylindrical body member.

* * * * *